(12) United States Patent
Zaragoza Doerwald et al.

(10) Patent No.: US 9,045,433 B2
(45) Date of Patent: Jun. 2, 2015

(54) METHOD FOR PREPARATION OF MEDETOMIDINE

(71) Applicant: LONZA LTD, Visp (CH)

(72) Inventors: Florencio Zaragoza Doerwald, Visp (CH); Anna Kulesza, Ausserberg (CH); Stephan Elzner, Brig-Glis (CH); Robert Bujok, Warsaw (PL); Zbigniew Wrobel, Warsaw (PL); Krzysztof Wojciechowski, Warsaw (PL)

(73) Assignee: Lonza Ltd., Visp (CH)

( * ) Notice: Subject to any disclaimer, the term of this patent is extended or adjusted under 35 U.S.C. 154(b) by 0 days.

(21) Appl. No.: 14/386,054

(22) PCT Filed: Nov. 15, 2012

(86) PCT No.: PCT/EP2012/072796
§ 371 (c)(1),
(2) Date: Sep. 18, 2014

(87) PCT Pub. No.: WO2013/011155
PCT Pub. Date: Jan. 24, 2013

(65) Prior Publication Data
US 2015/0057453 A1    Feb. 26, 2015

Related U.S. Application Data

(60) Provisional application No. 61/644,284, filed on May 8, 2012.

(30) Foreign Application Priority Data

May 8, 2012 (EP) .................................... 12167134
Oct. 22, 2012 (WO) ................ PCT/EP2012/070870
Nov. 14, 2012 (EP) .................................... 12192612

(51) Int. Cl.
*C07D 233/58* (2006.01)

(52) U.S. Cl.
CPC .................................. *C07D 233/58* (2013.01)

(58) Field of Classification Search
CPC .................................................. C07D 233/58
See application file for complete search history.

(56) References Cited

U.S. PATENT DOCUMENTS

| | | |
|---|---|---|
| 4,514,412 A | 4/1985 | Karjalainen et al. |
| 4,544,664 A | 10/1985 | Karjalainen et al. |
| 4,621,150 A | 11/1986 | Hirai et al. |
| 4,639,464 A | 1/1987 | Karjalainen et al. |
| RE32,400 E | 4/1987 | Karjalainen et al. |
| 4,826,864 A | 5/1989 | Karjalainen et al. |
| 6,313,354 B1 | 11/2001 | Markert et al. |
| 7,902,247 B2 | 3/2011 | Sinha et al. |
| 7,902,377 B2 | 3/2011 | Reine et al. |
| 8,735,438 B2 | 5/2014 | Sinha et al. |
| 2009/0176843 A1 | 7/2009 | Sinha et al. |
| 2010/0048915 A1 | 2/2010 | Reine et al. |
| 2011/0077274 A1 | 3/2011 | Sinha et al. |

FOREIGN PATENT DOCUMENTS

| | | |
|---|---|---|
| AU | 4822172 | 5/1974 |
| DE | 2252080 | 5/1973 |
| EP | 0058047 | 8/1982 |
| EP | 0153692 | 9/1985 |
| EP | 1918282 | 5/2008 |
| GB | 2101114 | 1/1983 |
| GB | 2453982 | 4/2009 |
| JP | S51-100041 | 9/1976 |
| JP | S51-100042 | 9/1976 |
| NL | 7214315 | 5/1973 |
| WO | WO 98/45237 | 10/1998 |
| WO | WO 00/42851 | 7/2000 |
| WO | WO 2009/089132 | 7/2009 |
| WO | WO 2011/070069 | 6/2011 |
| WO | WO 2012/172120 | 12/2012 |
| WO | WO 2013/011156 | 1/2013 |
| WO | WO 2013/011157 | 1/2013 |
| WO | WO 2013/011158 | 1/2013 |

OTHER PUBLICATIONS

EP Application No. 12167135.8 Extended Search Report, Sep. 25, 2012.
PCT/EP2012/070870 International Search Report and Written Opinion, Feb. 1, 2013.
PCT/EP2012/072796 International Search Report and Written Opinion, Feb. 1, 2013.
PCTIEP2012/072796 Written Opinion, Jun. 17, 2014.
PCT/EP2012/072796 International Preliminary Report on Patentability, Sep. 15, 2014.
PCT/EP2012/072797 Written Opinion, Feb. 1, 2013.
PCT/EP2012/072797 International Search Report, Feb. 1, 2013.
PCT/EP2012/072797 International 2014. Preliminary Report on Patentability, Apr. 25, 2014.
PCT/EP2012/072798 International Search Report and Written Opinion, Dec. 17, 2012.
PCT/EP2012/072799 International Search Report and Written Opinion, Mar. 20, 2013.
Cordi et al., Efficient Synthesis of (S)-4(5)-[1-2,3-Dimethylphenyl) ethyl]Imidazole Tartrate, the Potent $\alpha_2$ Adrenoreteptor Agonist Dexmedetomidine, Synthetic Communications, 26(8), pp. 1585-1593 (1996).
Huebner et al., Aconite alkaloids. XVI. Staphisine and the hydrocarbon obtained from its dehydrogenation, Journal of Biological Chemistry, vol. 169, pp. 211-220, (1947).
Mukherjee-Muller et al., 176, Säurekatalysierte Umlagerungen von 1,5.Dimethyl-6-methyliden-tricyclo[3.2.1.0   2,7]oct-3-en-8endo-olen, Helvetica Chimica Acta, vol. 60, Fasc. 5, pp. 1758-1780, (1977).
Zhang et al., Ultrasound-Promoted Synthesis of Substituted Phenanthrene-1,4-Quinones ; The Structure of Plectranthon D, Tetrahedron Letters, vol. 23, No. 14, pp. 2153-2156, (1994).

*Primary Examiner* — Rebecca Anderson
(74) *Attorney, Agent, or Firm* — Dority & Manning, P.A.

(57) ABSTRACT

The invention discloses a method for the preparation of medetomidine starting from 1-bromo 2,3-dimethylbenzene and aceton.

15 Claims, No Drawings

METHOD FOR PREPARATION OF MEDETOMIDINE

RELATED APPLICATIONS

This application is the national stage entry of International Patent Application No. PCT/EP2012/072796 having a filing date of Nov. 15, 2012, which claims the filing benefit of European Patent Application No. 12192612.5, having a filing date of Nov. 14, 2012, International Patent Application No. PCT/EP2012/070870, having a filing date of Oct. 22, 2012, U.S. Provisional Application No. 61/644,284, having a filing date of May 8, 2012, and European Patent Application No. 12167134.1, having a filing date of May 8, 2012, all of which are incorporated herein by reference in their entirety.

DESCRIPTION

The invention discloses a method for the preparation of medetomidine starting from 1-bromo 2,3-dimethylbenzene and acetone.

Medetomidine is the compound of formula (XX) and is an alpha2 adrenergic agonist, which is currently being used as veterinary sedative and analgesic and is evaluated as anesthetic.

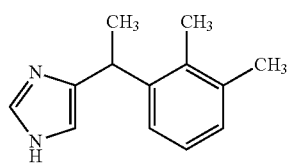

(XX)

Medetomidine is a 4-alkylimidazole. 4-Alkylimidazoles without additional substituents at the nitrogen moiety are usually mixtures of two tautomers. For instance, in the case of medetomidine, two tautomeric forms, represented by compound of formula (XX) and compound of formula (XX-T),

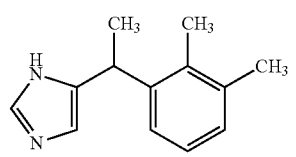

(XX-T)

will usually interconvert if medetomidine is dissolved or in a non-crystalline state. If one of the tautomeric forms prevails or if they are present in equal amounts is dependent on various factors, such as pH, solvent or temperature.

In the text, formula (XX) is used for medetomidine, and is meant to comprise both tautomeric forms as well as their mixture.

U.S. 2010/0048915 A discloses a method for the preparation of medetomidine by reaction of halogenated imidazoles with 2,3-dimethylbenzaldehyde using Grignard reagents. Cordi et al., Synth. Commun. 1996, 26, 1585-1593, discloses the preparation of medetomidine by reaction of 4-imidazolcarboxaldehyde with 2,3-dimethylphenylmagnesium bromide.

WO 00/42851 A discloses the use of medetomidine for inhibition of marine biofouling on surfaces.

The known methods of preparation of medetomidine often use protecting groups, for example triphenylmethyl (trityl) residues, which entails high material consumption and the need for protection/deprotection steps. Consequently, these syntheses are long and expensive. Furthermore rather expensive and non-readily available starting materials are used.

There was a need for a synthetic route, which does not need protecting groups, starts with less expensive substrates, avoids large amounts of waste and has satisfying yields.

In the following text, halogen means F, Cl, Br or I, preferably Cl, Br or I;

"alkyl" means linear or branched alkyl; if not otherwise stated. Examples of "alkyl" include methyl, ethyl, n-propyl, isopropyl, n-butyl, sec-butyl, tert-butyl, pentyl, hexyl, heptyl, and the like;

"cyclic alkyl" or "cyclo alkyl" are intended to include cyclo aliphatic, bicyclo aliphatic and tricycle aliphatic residues;

"alkane" means a linear or branched alkane;

"alkanol" means a hydroxyalkane, with alkane having the meaning as defined above also with its preferred embodiments;

Ac acetyl;

tBu tertiary butyl;

DBU 1,8-diazabicyclo[5.4.0]undec-7-ene;

DABCO 1,4-diazabicyclo[2.2.2]octane;

DIPEA N-ethyl-N,N-diisopropylamine;

DMA N,N-dimethylacetamide;

DMF N,N-dimethylformamide;

EDTA-Na$_2$ ethylene diamine tetraacetic acid disodium;

hexanes mixture of isomeric hexanes;

NMP N-methyl-2-pyrrolidone;

OTf trifluoromethanesulfonate, also known as triflate;

MPS KHSO$_5$, also known as potassium peroxymonosulfate or potassium monopersulfate, and marketed as a triple salt with the formula 2 KHSO$_5$ KHSO$_4$ K$_2$SO$_4$ under the trade names Caroat® and Oxone®, therefore KHSO$_5$ is often used in form of this triple salt;

salen ligand obtained from a condensation of salicylaldehyde or of a substituted salicylaldehyde derivative with ethylene diamine or with a substituted ethylene diamine;

sulfamic acid HO—SO$_2$—NH$_2$;

TEMPO 2,2,6,6-tetramethylpiperidine 1-oxyl;

THF tetrahydrofuran;

xylene 1,2-dimethylbenzene, 1,3-dimethylbenzene, 1,4-dimethylbenzene or a mixture thereof;

if not otherwise stated.

Subject of the invention is a method for preparation of medetomidine, the method comprises a step (N) and a step (M1);

step (M1) comprises a reaction (M1-reac);

reaction (M1-reac) is a reaction between a compound selected from the group consisting of compound of formula (XXI), the hydrate of compound of formula (XXI) and a hemiacetal of compound of formula (XXI),

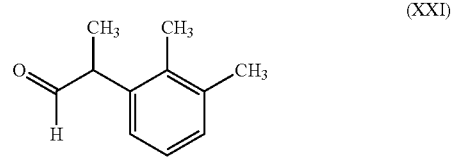

(XXI)

said hemiacetal of compound of formula (XXI) being the product of an addition reaction between the aldehyde as depicted in formula (XXI) and an alcohol selected from the group consisting of tert-butanol and isopropanol,
and a reagent (M-reag) and a reagent (M-A) in a solvent (M-solv);
reagent (M-reag) is selected from the group consisting of p-toluenesulfonylmethyl isocyanide, trifluoromethanesulfonylmethyl isocyanide, methanesulfonylmethyl isocyanide, benzenesulfonylmethyl isocyanide, 4-acetamidobenzenesulfonylmethyl isocyanide and mixtures thereof;
reagent (M-A) is selected from the group consisting of ammonia, sulfamic acid, p-toluenesulfonamide, benzenesulfonamide, 4-acetamidobenzenesulfonamide, tritylamine, formamide, urea, urotropine, ethyl carbamate, acetamide and mixtures thereof;
solvent (M-solv) is selected from the group consisting of N,N-dimethylformamide, $C_{1-6}$ alkanol, formamide, 1,2-dimethoxyethane, NMP, toluene, acetonitrile, propionitrile, ethyl carbamate, N,N-dimethylacetamide, water, acetamide and mixtures thereof;
and wherein compound of formula (XXI) is prepared in the step (N);
step (N) comprises a reaction (N-reac);
reaction (N-reac) is a reaction of compound of formula (XXII) with a catalyst (N-cat);

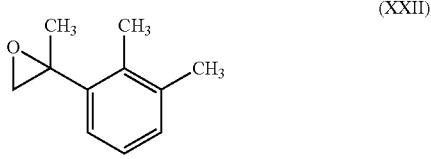

(XXII)

catalyst (N-cat) is selected from the group consisting of acetic acid, formic acid, trifluoroacetic acid, methanesulfonic acid, benzenesulfonic acid, p-toluenesulfonic acid, camphorsulfonic acid, HCl, HBr, $H_2SO_4$, $HNO_3$, $H_3PO_4$, $HClO_4$, $BCl_3$, $BBr_3$, $BF_3OEt_2$, $BF_3SMe_2$, $BF_3THF$, $MgCl_2$, $MgBr_2$, $MgI_2$, $AlCl_3$, $Al(O-C_{1-4}$ alkyl$)_3$, $SnCl_4$, $TiCl_4$, $Ti(O-C_{1-4}$ alkyl$)_4$, $ZrCl_4$, $Bi_2O_3$, $BiCl_3$, $ZnCl_2$, $PbCl_2$, $FeCl_3$, $ScCl_3$, $NiCl_2$, $Yb(OTf)_3$, $Yb(Cl)_3$, $GaCl_3$, $AlBr_3$, $Ce(OTf)_3$, LiCl, $Cu(BF_4)_2$, $Cu(OTf)_2$, $NiBr_2(PPh_3)_2$, $NiBr_2$, $NiCl_2$, $Pd(OAc)_2$, $PdCl_2$, $PtCl_2$, $InCl_3$, acidic inorganic solid substance, acidic ion exchange resin, carbon treated with inorganic acid and mixtures thereof.
Preferably, reagent (M-reag) is selected from the group consisting of p-toluenesulfonylmethyl isocyanide, benzenesulfonylmethyl isocyanide and mixtures thereof;
more preferably, reagent (M-reag) is p-toluenesulfonylmethyl isocyanide.
Preferably, reagent (M-A) is selected from the group consisting of ammonia, sulfamic acid, p-toluenesulfonamide, benzenesulfonamide, 4-acetamidobenzenesulfonamide, tritylamine, formamide and mixtures thereof;
more preferably, reagent (M-A) is selected from the group consisting of ammonia, p-toluenesulfonamide, benzenesulfonamide, formamide, 4-acetamidobenzenesulfonamide, tritylamine and mixtures thereof;
even more preferably, reagent (M-A) is selected from the group consisting of ammonia, p-toluenesulfonamide, formamide, and mixtures thereof;
especially, reagent (M-A) is ammonia or formamide.
Preferably, solvent (M-solv) is selected from the group consisting of N,N-dimethylformamide, methanol, ethanol, n-propanol, isopropanol, butanol, pentanol, hexanol, water, formamide, 1,2-dimethoxyethane, NMP, toluene, acetonitrile, propionitrile, ethyl carbamate, N,N-dimethylacetamide, acetamide and mixtures thereof;
more preferably, solvent (M-solv) is selected from the group consisting of N,N-dimethylformamide, methanol, ethanol, ethyl carbamate, formamide, acetamide and mixture thereof.
Preferably, reaction (M1-reac) is done in the presence of a compound (M-comp), compound (M-comp) is selected from the group consisting of ammonia, tritylamine, NaCN, KCN, piperidine, DBU, DABCO, triethylamine, tributylamine, 4-dimethylaminopyridine, pyridine, tBuOK, tBuONa, $NaHCO_3$, $Na_2CO_3$, $(NH_4)HCO_3$, $(NH_4)_2CO_3$, $KHCO_3$, $K_2CO_3$, NaOAc, KOAc, NaOH, KOH, $Ca(OH)_2$, KF and mixtures thereof;
preferably, compound (M-comp) is selected from the group consisting of ammonia, tritylamine, NaCN, KCN, piperidine, tBuOK, tBuONa, KOH, $K_2CO_3$, $Na_2CO_3$, KF and mixtures thereof;
more preferably, compound (M-comp) is selected from the group consisting of ammonia, NaCN, KCN, piperidine, tBuOK, tBuONa, $K_2CO_3$, $Na_2CO_3$, KF and mixtures thereof;
even more preferably, compound (M-comp) is selected from the group consisting of ammonia, NaCN, $K_2CO_3$, tBuOK, tBuONa, $Na_2CO_3$ and mixtures thereof;
especially, compound (M-comp) is selected from the group consisting of ammonia, NaCN, tBuOK, tBuONa, $Na_2CO_3$ and mixtures thereof;
more especially, compound (M-comp) is NaCN or ammonia.
The reagent (M-A) can be used as such or in form of a solution in a solvent (M-A). Solvent (M-A) is identical or different from solvent (M-solv), preferably identical, and comprises the same group of solvents as solvent (M-solv), also with respect to all of the preferred embodiments of solvent (M-solv).
When reagent (M-A) is ammonia, then reagent (M-A) is preferably used in form of a solution, preferably in form of a solution in methanol.
In case of ethyl carbamate, formamide and acetamide, reagent (M-A) can be identical with solvent (M-solv) and can be used as solvent (M-solv).
Preferably, the reaction temperature of reaction (M1-reac) is from −10 to 250° C., more preferably from 0 to 200° C., even more preferably from 10 to 180° C.
The reaction (M1-reac) can be done in a system, that is closed or open to the atmosphere; preferably the reaction (M1-reac) is done in a closed system.
In a closed system, the pressure depends mainly on the boiling point of the solvent (M-solv), on the amount of ammonia used, and on the reaction temperature of reaction (M1-reac);
preferably, the reaction (M1-reac) is done at a pressure of from atmospheric pressure to 20 bar, more preferably of from atmospheric pressure to 10 bar, even more preferably of from atmospheric pressure to 5 bar.
Preferably, the reaction time of reaction (M1-reac) is from 30 min to 72 h, more preferably from 1 h to 48 h, even more preferably from 2 h to 24 h.
Reaction (M1-reac) may be conducted at a constant temperature, or the temperature may be modified during the progress of the reaction. For instance, the reaction may be run for a certain time at first temperature, and then for a given time at second temperature different from the first temperature; alternatively, the temperature may be modified continuously during the reaction.
Preferably, from 1.0 to 10 mol equivalents, more preferably from 1.1 to 5 mol equivalents, even more preferably from 1.1 to 3 mol equivalents of reagent (M-reag) are used, the mol equivalents being based on the mol of compound of formula (XXI).

When one or more reagents (M-A) different from ammonia, formamide and ethyl carbamate are used, the total amount of substances different from ammonia, formamide and ethyl carbamate used as reagent (M-A) is preferably from 1.0 to 10 mol equivalents, more preferably from 1.1 to 5 mol equivalents, even more preferably from 1.1 to 3 mol equivalents, the mol equivalents being based on the mol of compound of formula (XXI).

When ammonia, formamide, ethyl carbamate or mixtures thereof are used as reagent (M-A), preferably from 1.0 to 100 mol equivalents, more preferably from 1.1 to 50 mol equivalents, even more preferably from 1.1 to 30 mol equivalents of ammonia, formamide, ethyl carbamate or mixtures thereof are used, the mol equivalents being based on the mol of compound of formula (XXI).

When one or more substances selected from the group ammonia, formamide and ethyl carbamate, and one or more substances different from ammonia, formamide and ethyl carbamate are used as reagent (M-A), the given amounts for ammonia, formamide and ethyl carbamate, and the given amounts for the one or more substances different from ammonia, formamide and ethyl carbamate, add up to the total amount of reagent (M-A); the total amount of reagent (M-A) is preferably from 1.0 to 100 mol equivalents, more preferably from 1.1 to 50 mol equivalents, even more preferably from 1.1 to 30 mol equivalents, the mol equivalents being based on the mol of compound of formula (XXI).

Preferably from 1 to 15 mol equivalents, more preferably from 1 to 10 mol equivalents, even more preferably from 1 to 5 mol equivalents of compound (M-comp) are used, the mol equivalents being based on the mol of compound of formula (XXI).

Preferably, the amount of solvent (M-solv) is from 0.5 to 20 fold, more preferably from 1 to 10 fold, even more preferably of from 2 to 5 fold, of the weight of compound of formula (XXI).

Preferably, the reaction (M1-reac) is done under inert atmosphere.

When tritylamine is used as reagent (M-A), the product of reaction (M1-reac) may be N-trityl medetomidine and the trityl residue would have to be removed.

Preferably in this case, the method for preparation of medetomidine comprises a further step (M2); step (M2) is done after step (M1); step (M2) comprises a reaction (M2-reac); reaction (M2-reac) is the treatment of the product of reaction (M1-reac) with an acid (M-acid detrit). Acid (M-acid detrit) is preferably selected from the group consisting of acetic acid, propionic acid, formic acid, HCl or mixtures thereof. Acid (M-acid detrit) can be used as an aqueous solution.

Any sequence of the reaction of reagent (M-reag) and of reagent (M-A) with the compound of formula (XXI) in reaction (Ml-reac) can be used:
compound of formula (XXI) can first be reacted with reagent (M-reag) and then reagent (M-A) added; or
compound of formula (XXI) can first be reacted with reagent (M-A) and then reagent (M-reag) added; or
compound of formula (XXI) can simultaneously be reacted with reagent (M-reag) and with reagent (M-A), this embodiment is preferably suited for the case that reagent (M-A) and solvent (M-solv) are identical and are formamide, ethyl carbamate or acetamide; preferably formamide.

Preferably, compound of formula (XXI) is first reacted with reagent (M-reag) and then reagent (M-A) added; or
compound of formula (XXI) is simultaneously reacted with reagent (M-reag) and with reagent (M-A).

Step (M1) can therefore be done in three alternatives, the three alternatives are alternative (M1-A1), alternative (M1-A2) and alternative (M1-A3).

Alternative (M1-A1) comprises two steps, a step (M1-A1-1) and a step (M1-A1-2);
step (M1-A1-1) comprises a reaction (M1-A1-1);
reaction (M1-A1-1) is a reaction of compound of formula (XXI) with reagent (M-reag) in the presence of compound (M-comp) and in a solvent (M-solv);
step (M1-A1-2) comprises a reaction (M1-A1-2).
reaction (M1-A1-2) is a reaction of the reaction product of reaction (M1-A1-1) with reagent (M-A) in the presence of compound (M-comp) and in a solvent (M-solv).

Preferably, the reaction temperature of reaction (M1-A1-1) is from −10 to 250° C., more preferably from 0 to 200° C., even more preferably from 10 to 180° C.

Preferably, the reaction temperature of reaction (M1-A1-2) is from 20 to 250° C., more preferably from 50 to 200° C., even more preferably from 80 to 180° C.

Preferably from 0.01 to 1 mol equivalents, more preferably from 0.1 to 0.5 mol equivalents, even more preferably from 0.2 to 0.3 mol equivalents of compound (M-comp) are used in reaction (M1-A1-1), the mol equivalents being based on the mol of compound of formula (XXI).

Preferably from 1 to 10 mol equivalents, more preferably from 1 to 5 mol equivalents, even more preferably from 1 to 3 mol equivalents of compound (M-comp) are used in reaction (M1-A1-2), the mol equivalents being based on the mol of compound of formula (XXI).

Alternative (M1-A2) comprises two steps, a step (M1-A2-1) and a step (M1-A2-2);
step (M1-A2-1) comprises a reaction (M1-A2-1);
reaction (M1-A2-1) is a reaction of compound of formula (XXI) with reagent (M-A) in a solvent (M-solv);
step (M1-A2-2) comprises a reaction (M1-A2-2).
reaction (M1-A2-2) is a reaction of the reaction product of reaction (M1-A2-1) with reagent (M-reag) in the presence of compound (M-comp) and in a solvent (M-solv).

Preferably, the reaction temperature of reaction (M1-A2-1) is from 0 to 250° C., more preferably from 10 to 200° C., even more preferably from 20 to 180° C.

Preferably, the reaction temperature of reaction (M1-A2-2) is from −10 to 250° C., more preferably from 0 to 200° C., even more preferably from 20 to 180° C.

In case of reagent (M-A) not being ammonia and tritylamine, reaction (M1-A2-1) can be done in the presence of an acid (M1-A2-1); acid (M1-A2-1) is selected from the group consisting of p-toluenesulfonic acid, methanesulfonic acid and benzenesulfonic acid;
preferably from 0.01 to 1 mol equivalents, more preferably from 0.05 to 0.5 mol equivalents, even more preferably from 0.1 to 0.3 mol equivalents of acid (M1-A2-1) are used in reaction (M1-A2-1), the mol equivalents being based on the mol of compound of formula (XXI).

Preferably from 1 to 10 mol equivalents, more preferably from 1 to 5 mol equivalents, even more preferably from 1 to 3 mol equivalents of compound (M-comp) are used in reaction (M1-A2-2), the mol equivalents being based on the mol of compound of formula (XXI).

Alternative (M1-A3) comprises a step (M1-A3-1)
step (M1-A3-1) comprises a reaction (M1-A3-1);
reaction (M1-A3-1) is a reaction of compound of formula (XXI) with reagent (M-reag) and with with reagent (M-A) in a solvent (M-solv).

Preferably, the reaction temperature of reaction (M1-A3-1) is from 0 to 250° C., more preferably from 20 to 200 ° C., even more preferably from 50 to 180° C.

Reaction (M1-A3-1) can be done in the presence of compound (M-comp); preferably from 1 to 10 mol equivalents, more preferably from 1 to 5 mol equivalents, even more preferably from 1 to 3 mol equivalents of compound (M-comp) are used in reaction (M1-A3-1), the mol equivalents being based on the mol of compound of formula (XXI).

In case of all these three alternatives, reagent (M-reag), reagent (M-A), compound (M-comp) and solvent (M-solv) are as defined herein, also with all their preferred embodiments.

When the reaction (M1-reac) is completed, medetomidine can be isolated by standard methods such as evaporation of volatile components, extraction, washing, drying, concentration, filtration, crystallization, distillation, chromatography and any combination thereof.

Preferably, the volatile components of the reaction mixture are removed by evaporation under reduced pressure.

Preferably, the reaction mixture resulting from reaction (M1-reac) or the reaction mixture resulting from reaction (M2-reac) can be extracted with a solvent (M-extract), solvent (M-extract) is preferably selected from the group consisting of water, toluene, benzene, xylene, chlorobenzene, dichloromethane, chloroform, acetic acid $C_{1-8}$ alkyl ester and combinations thereof;
the acetic acid $C_{1-8}$ alkyl ester is preferably an acetic acid $C_{1-4}$ alkyl ester, more preferably selected from the group consisting of ethyl acetate, isopropyl acetate and butyl acetate;
preferably solvent (M-extract) is selected from the group consisting of toluene, dichloromethane, ethyl acetate, isopropyl acetate and mixtures thereof. The extraction can be followed by filtration and concentration of the extract.

Preferably, after an extraction with a solvent (M-extract), the extract resulting from the extraction with solvent (M-extract) can be extracted with an aqueous solution of an acid (M-acid). Acid (M-acid) is preferably selected from the group consisting of oxalic acid, citric acid, maleic acid, fumaric acid, tartaric acid, $NH_4Cl$, HCl, HBr, $H_2SO_4$, $H_3PO_4$ and mixtures thereof.

The extract resulting from the extraction with an aqueous solution of acid (M-acid) can be washed with a solvent (M-wash).

Preferably, solvent (M-wash) is selected from the group consisting of toluene, benzene, xylene, chlorobenzene, dichloromethane, chloroform, acetic acid $C_{1-8}$ alkyl ester and mixtures thereof; the acetic acid $C_{1-8}$ alkyl ester is preferably an acetic acid $C_{1-4}$ alkyl ester, more preferably selected from the group consisting of ethyl acetate, isopropyl acetate and, butyl acetate.

The product can be isolated by concentration of the extract, that was washed with solvent (M-wash).

In another preferred embodiment, the reaction mixture resulting from reaction (M1-reac) or the reaction mixture resulting from reaction (M2-reac) can be, without above mentioned extraction with solvent (M-extract), acidified by mixing with an aqueous solution of acid (M-acid). The mixture, that is thereby obtained, can be washed with solvent (M-wash), and the product can be isolated by concentration.

If the deprotonated medetomidine is to be isolated, a suspension or solution of the salt of medetomidine, preferably an aqueous suspension or solution of the salt of medetomidine, can be basified by addition of a base (M-basify) or of an aqueous solution of base (M-basify);
preferably base (M-basify) is selected from the group consisting of $NaHCO_3$, $Na_2CO_3$, NaOH and mixtures thereof.

Preferably, base (M-basify) is added in such an amount, that the pH of the resulting mixture is from 7 to 12, more preferably from 8 to 10, even more preferably from 8 to 9.

After the addition of base (M-basify), an aqueous phase can be extracted with solvent (M-extract), followed by isolation of the product by concentration of the extract.

Preferably, any washing of any organic phase after reaction (M1-reac) or after reaction (M2-reac) can be done with water, with base (M-basify), with an aqueous solution of base (M-basify) or with brine.

Preferably, any extraction of any aqueous phase after reaction (M1-reac) or after reaction (M2-reac) is done with solvent (M-extract).

Preferably, the reaction mixture after reaction (M1-reac) or after reaction (M2-reac) is first concentrated under reduced pressure, then diluted with water and acidified with acid (M-acid) as described above, washed with solvent (M-wash), preferably solvent (M-wash) is toluene, basified with base (M-basify), preferably base (M-basify) is an aqueous solution of $NaHCO_3$, and then extracted with solvent (M-extract), preferably solvent (M-extract) is selected from the group consisting of toluene, dichloromethane, isopropyl acetate and ethyl acetate; followed by isolation of the product by concentration of the extract.

In another preferred embodiment, medetomidine is purified after reaction (M1-reac) or after reaction (M2-reac) by chromatography.

Any organic phase can be dried, preferably over $MgSO_4$ or $Na_2SO_4$.

Any concentration is preferably done by distillation, preferably under reduced pressure.

Medetomidine can be purified, preferably by crystallization or distillation under reduced pressure, more preferably by crystallization from a mixture of cyclohexane and toluene, even more preferably from cyclohexane:toluene 99:1 vv.

Medetomidine may also be converted into a salt by mixing with an acid (M-acid salt), acid (M-acid salt) is preferably used as aqueous solution, acid (M-acid salt) is preferably selected from the group consisting of acetic acid, oxalic acid, HCl and $H_2SO_4$;
then it can be isolated by filtration and purified by recrystallization in a solvent (M-cryst), solvent (M-cryst) is preferably selected from the group consisting of water, ethanol, methanol, isopropanol, acetonitrile, hexane, cyclohexane, heptane, toluene, ethyl acetate and mixtures thereof; recrystallization can be repeated using a different solvent (Mcryst).

Preferably, the acidic inorganic solid substance is aluminosilicates.

Preferably, the acidic ion exchange resin is selected from the group consisting of copolymers of styrene and divinylbenzene and of perfluorinated branched or linear polyethylenes, these polymers being functionalized with $SO_3H$ groups; more preferably, the acidic ion exchange resin is selected
  from the group consisting of copolymers of styrene and divinylbenzene containing more than 5% of divinylbenzene, preferably being macroreticular, and of perfluorinated polyethylenes, these polymers being functionalized with $SO_3H$ groups.

Preferably, the inorganic acid, with which the carbon was treated, is selected from the group consisting of HCl, $H_2SO_4$ and $HNO_3$.

Preferably, the catalyst (N-cat) is selected from the group consisting of acetic acid, formic acid, trifluoroacetic acid, methanesulfonic acid, p-toluenesulfonic acid, HCl, HBr, $H_2SO_4$, $H_3PO_4$, $BCl_3$, $BF_3OEt_2$, $MgCl_2$, $MgBr_2$, $AlCl_3$, $ZnCl_2$, $Cu(BF_4)_2$, aluminosilicates, acidic ion exchange resins, carbon treated with HCl, $H_2SO_4$ or $HNO_3$, and mixtures thereof;

more preferably, the catalyst (N-cat) is selected from the group consisting of acetic acid, formic acid, methanesulfonic acid, p-toluenesulfonic acid, HCl, $H_2SO_4$, $BF_3OEt_2$, $Cu(BF_4)_2$, aluminosilicates, acidic ion exchange resins, and mixtures thereof.

Preferably, reaction (N-reac) is done in a solvent (N-solv); solvent (N-solv) is selected from the group consisting of water, tert-butanol, isopropanol, acetonitrile, propionitrile, THF, methyl-THF, NMP, dioxane, 1,2-dimethoxyethane, dichloromethane, 1,2-dichloroethane, chloroform, toluene, benzene, chlorobenzene, hexane, cyclohexane, ethyl acetate, acetic acid, formic acid, trifluoroacetic acid and mixtures thereof;

preferably from water, acetonitrile, propionitrile, THF, 2-methyl-THF, 1,2-dimethoxyethane, dichloromethane, 1,2-dichloroethane, chloroform, toluene, cyclohexane, ethyl acetate, acetic acid, formic acid and mixtures thereof;

more preferably from water, acetonitrile, propionitrile, THF, 2-methyl-THF, 1,2-dimethoxyethane, dichloromethane, 1,2-dichloroethane, toluene, ethyl acetate and mixtures thereof;

even more preferably from acetonitrile, THF, 2-methyl-THF, dichloromethane, toluene, ethyl acetate and mixtures thereof.

The catalyst (N-cat) can be used in a pure form or as hydrate.

The catalyst (N-cat) can be used as a solution in solvent (N-solv).

Preferably, the molar ratio between catalyst (N-cat) and compound of formula (XXII) is from 1:1000 to 10:1, more preferably from 1:100 to 5:1, even more preferably from 1:20 to 1:1, especially from 1:10 to 1:2.

Preferably, the reaction temperature of reaction (N-reac) is from −20 to 200° C., more preferably from 0 to 150 ° C., even more preferably from 10 to 100° C.

The reaction (N-reac) can be done in a system, that is closed or open to the atmosphere. In a closed system, the pressure depends mainly on the boiling point of a solvent (N-solv) and on the reaction temperature of reaction (N-reac).

Preferably, the reaction (N-reac) is done at a pressure of from 0.01 bar to 20 bar, more preferably of from 0.1 to 10 bar, even more preferably of from atmospheric pressure to 5 bar. More preferably, the reaction (N-reac) is done in an open system.

Preferably, the reaction time of reaction (N-reac) is from 30 min to 72 h, more preferably from 1 h to 48 h, even more preferably from 2 h to 24 h.

Alternatively, reaction (N-reac) can be done as a continuous gas-phase reaction by passing the evaporated compound of formula (XXII) over the catalyst (N-cat). This gas-phase reaction can be done in the presence of an inert gas, the inert gas is preferably selected from the group consisting of nitrogen, a noble gas and carbon dioxide.

After reaction (N-reac), compound of formula (XXI) can be isolated by standard methods such as evaporation of volatile components, extraction, washing, drying, concentration, filtration, crystallization, distillation, chromatography and any combination thereof.

Compound of formula (XXI) can be obtained in step (N) as the aldehyde as depicted in formula (XXI), but also in form of its hydrate or hemiacetal. The hemiacetal of compound of formula (XXI), which can result as product from step (N), can be the product of an addition reaction between the aldehyde as depicted in formula (XXI) and an alcohol selected from the group consisting of tert-butanol and isopropanol. Also this hydrate and this hemiacetal can be directly used in step (M1).

When compound of formula (XXI) is obtained from reaction (N-reac) in form of its hydrate or of a hemiacetal, the hydrate or the hemiacetale can be converted into the aldehyde by standard reactions known to the person skilled in the art.

Preferably, compound of formula (XXII) is prepared in a step (O) or in two steps, the two steps are step (O1) and step (O2);

step (O) comprises a reaction (O-reac);
reaction (O-reac) is a reaction of compound of formula (XXIII), with a reagent (O-reag);

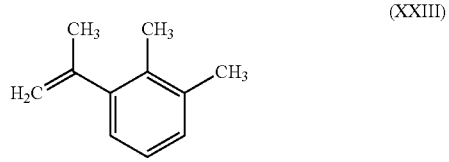

(XXIII)

reagent (O-reag) is selected from the group consisting of peracetic acid, trifluoroperacetic acid, perbenzoic acid, 3-chloroperbenzoic acid, monoperphthalic acid, dimethyldioxirane, tert-butylhydroperoxide, dibenzoyl peroxide, cumenehydroperoxide, oxygen, air, sodium hypochlorite, $KHSO_5$, $Na_2O_2$, aqueous $H_2O_2$, $H_2O_2$ dissolved in acetic acid, $H_2O_2$ dissolved in trifluoroacetic acid, and mixtures thereof;

step (O1) comprises a reaction (O1-reac);
reaction (O1-reac) is a reaction of compound of formula (XXIII) with water and with a compound (O1-comp);
compound (O1-comp) is selected from the group consisting of bromine, N-bromosuccinimide, chlorine, N-chlorosuccinimide, iodine, N-iodosuccinimide, IBr, BrCl, and mixtures thereof;

step (O2) comprises a reaction (O2-reac);
reaction (O2-reac) is a reaction of the reaction product from reaction (O1-reac) with a base (O2-base);
base (O2-base) is selected from the group consisting of sodium hydroxide, potassium hydroxide, calcium hydroxide and mixture thereof.

Preferably, reagent (O-reag) is selected from the group consisting of peracetic acid, tert-butylhydroperoxide, oxygen, air, sodium hypochlorite, aqueous $H_2O_2$, $H_2O_2$ dissolved in acetic acid, $H_2O_2$ dissolved in trifluoroacetic acid, and mixtures thereof;

more preferably, reagent (O-reag) is aqueous $H_2O_2$.

Preferably, reaction (O-reac) is done in a solvent (O-solv);
solvent (O-solv) is selected from the group consisting of water, aqueous solutions of $NaHCO_3$, $Na_2CO_3$, $(NH_4)HCO_3$, $(NH_4)_2CO_3$, $KHCO_3$ or $K_2CO_3$, benzene, toluene, NMP, dioxane, acetone, ethyl acetate, methylethylketone, tert-butanol, acetonitrile, chloroform, dichloromethane and mixtures thereof;

preferably from water, aqueous solutions of $NaHCO_3$, $Na_2CO_3$, $KHCO_3$ or $K_2CO_3$, toluene, dioxane, acetone, ethyl acetate, methylethylketone, tert-butanol, acetonitrile, dichloromethane and mixtures thereof.

Reaction (O-reac) can be done in the presence of a catalyst (O-cat);

catalyst (O-cat) is selected from the group consisting of trifluoroacetic acid, trifluoroacetone, Mn(salen) complex, aldehydes, N-methylmorpholine N-oxide, 2,2,6,6-tetramethylpiperidine 1-oxyl and mixtures thereof;
aldehydes are preferably isobutyraldehyde or benzaldehyde.

Reaction (O-reac) can be done in the presence of a buffer (O-buf);
preferably, buffer (O-buf) is an aqueous buffer and is selected from the group consisting of $K_2CO_3$/EDTA-$Na_2$ buffer, phosphate buffer and other buffers known by the skilled person;
more preferably, buffer (O-buf) is an $K_2CO_3$/EDTA-$Na_2$ buffer.

Preferably, the reaction temperature of reaction (O-reac) is from –20 to 100° C., more preferably from –10 to 80° C., even more preferably from 0 to 50° C.

The reaction (O-reac) can be done in a system, that is closed or open to the atmosphere. In a closed system, the pressure depends on the boiling point of a solvent (O-solv) and on the reaction temperature of reaction (O-reac).

Preferably, the reaction (N-reac) is done at a pressure of from 0.01 bar to 20 bar, more preferably of from 0.1 to 10 bar, even more preferably of from atmospheric pressure to 5 bar. More preferably the reaction (O-reac) is done in an open system.

Preferably, the reaction time of reaction (O-reac) is from 30 min to 72 h, more preferably from 1 h to 48 h, even more preferably from 2 h to 24 h.

After the reaction (O-reac), the compound of formula (XXII) can be isolated by standard methods such as evaporation of volatile components, extraction, washing, drying, concentration, crystallization, distillation, chromatography and any combination thereof.

Preferably, reaction (O1-reac) and reaction (O2-reac) are conducted in solvent (O-solv), with solvent (O-solv) as defined above, also with all its preferred embodiments.

Preferably, the reaction temperatures of reaction (O1-reac) and of reaction (O2-reac) are identical or different and independently from each other from –20 to 100° C., more preferably from –10 to 80° C., even more preferably from 0 to 50° C.

Reaction (O1-reac) and reaction (O2-reac) can independently from each other be done in systems, that are closed or open to the atmosphere.

In a closed system, the pressure depends on the boiling point of a solvent (O-solv) and on the reaction temperature of reaction (O1-reac) and reaction (O-reac) respectively.

Preferably, reaction (O1-reac) and reaction (O2-reac) are independently from each other done at pressures of from 0.01 bar to 20 bar, more preferably of from 0.1 to 10 bar, even more preferably of from atmospheric pressure to 5 bar.

More preferably, reaction (O1-reac) and reaction (O2-reac) are done in a open system.

Preferably, the reaction times of reaction (O1-reac) and of reaction (O2-reac) are independently from each other from 30 min to 72 h, more preferably from 1 h to 48 h, even more preferably from 2 h to 24 h.

The reaction product of reaction (O1-reac) and the compound of formula (XXII) from reaction (O2-reac) can be isolated by standard methods such as evaporation of volatile components, extraction, washing, drying, concentration, filtration, crystallization, distillation, chromatography and any combination thereof.

Reaction (O1-reac) and reaction (O2-reac) can be done consecutively without isolation of the reaction product of reaction (O1-reac), they can be done in one pot.

Preferably, compound of formula (XXII) is not isolated, step (N) is done directly after step (O) or step (O2) respectively in one pot. For this, catalyst (N-cat) is simply added to the reaction mixture resulting from reaction (O-reac) or from reaction (O2-reac) respectively.

Preferably, compound of formula (XXIII) is prepared in a step (P);
step (P) comprises a reaction (P-reac);
in reaction (P-reac) the compound of formula (XXIV) is exposed to a temperature (P-temp);

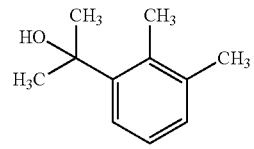
(XXIV)

temperature (P-temp) is from 0 to 300° C.

Preferably, temperature (P-temp) is from 5 to 200° C., more preferably from 100 to 150° C.

Reaction (P-reac) can be done in a solvent (P-solv);
solvent (P-solv) is selected from the group consisting of benzene, toluene, xylene, hexane, heptane, 1,2-dichloroethane, NMP, dichloromethane, chloroform and mixtures thereof;
preferably from benzene, toluene, xylene, dichloromethane and mixtures thereof.

Preferably, reaction (P-reac) is done in the presence of a catalyst (P-cat);
catalyst (P-cat) is selected from the group consisting of acetic acid, formic acid, trifluoroacetic acid, methanesulfonic acid, benzenesulfonic acid, p-toluenesulfonic acid, camphorsulfonic acid, HCl, HBr, $H_2SO_4$, KOH, NaOH, $KHSO_4$, $HNO_3$, $H_3PO_4$, $HClO_4$, $BCl_3$, $BBr_3$, $BF_3OEt_2$, $BF_3SMe_2$, $BF_3THF$, $MgCl_2$, $MgBr_2$, $MgI_2$, $AlCl_3$, Al(O—$C_{1-4}$ alkyl)$_3$, $I_2$, $Al_2O_3$, $SnCl_4$, $TiCl_4$, Ti(O—$C_{1-4}$ alkyl)$_4$, $ZrCl_4$, $Bi_2O_3$, $BiCl_3$, $ZnCl_2$, $PbCl_2$, $FeCl_3$, Yb(OTf)$_3$, Yb(Cl)$_3$, $GaCl_3$, $AlBr_3$, Ce(OTf)$_3$, LiCl, acidic insoluble inorganic solid, acidic ion exchange resins, carbon treated with an inorganic acid, and mixtures thereof;
preferably from methanesulfonic acid, benzenesulfonic acid, p-toluenesulfonic acid, $H_2SO_4$, $KHSO_4$, $H_3PO_4$, acidic insoluble inorganic solid, acidic ion exchange resins, carbon treated with an inorganic acid, and mixtures thereof.

Preferably, the acidic insoluble inorganic solid is acidic aluminosilicates or silica gel.

Preferably, the inorganic acid, with which the carbon was treated, is selected from the group consisting of HCl, $H_2SO_4$ and $HNO_3$.

Preferably, the acidic ion exchange resin is selected from the group consisting of copolymers of styrene and divinylbenzene and of perfluorinated branched or linear polyethylenes, these polymers being functionalized with $SO_3H$ groups;
more preferably, the acidic ion exchange resin is selected from the group consisting of copolymers of styrene and divinylbenzene containing more than 5% of divinylbenzene, preferably being macroreticular, and of perfluorinated polyethylenes, these polymers being functionalized with $SO_3H$ groups.

When reaction (P-reac) is done in the presence of a catalyst (P-cat), temperature (P-temp) is preferably from 0 to 200° C., more preferably from 10 to 150° C., even more preferably from 10 to 100° C.

Reaction (P-reac) can be done in gas phase by passing evaporated compound of formula (XXIV) through a heated tube, the heated tube can be charged with a catalyst (P-cat).

After reaction (P-reac), the compound of formula (XXIII) can be isolated by standard methods such as evaporation of volatile components, extraction, washing, drying, concentration, crystallization, distillation, chromatography and any combination thereof.

Preferably, compound of formula (XXIV) is prepared in three steps, the three steps are a step (Q1), a step (Q2) and a step (Q3);

step (Q1) comprises a reaction (Q1-reac) by a reaction of compound of formula (XXV) with a reagent (Q1-reag);

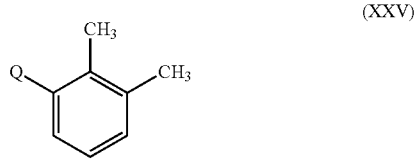

(XXV)

Q is Br, Cl, or I;
reagent (Q1-reag) is selected from the group consisting of lithium, magnesium, aluminum, zinc, calcium, isopropylmagnesium chloride, isopropylmagnesium bromide, butyllithium, sec-butyllithium and mixtures thereof;
step (Q2) comprises a reaction (Q2-reac);
reaction (Q2-reac) is a reaction of the reaction product of reaction (Q1-reac) with acetone;
in step (Q3) comprises a reaction (Q3-reac);
reaction (Q3-reac) is a reaction of the reaction product of reaction (Q2-reac) with a reagent (Q3-reag);
reagent (Q3-reag) is selected from the group consisting of water, methanol, ethanol, oxalic acid, citric acid, $NH_4Cl$, HCl, HBr, $HNO_3$, $H_2SO_4$, $H_3PO_4$, acetic acid, propionic acid, formic acid and mixtures thereof.

Preferably, Q is Br.

Preferably, reagent (Q1-reag) is selected from the group consisting of lithium, magnesium, aluminum, isopropylmagnesium chloride, isopropylmagnesium bromide and mixtures thereof.

Reaction (Q1-reac) can be catalyzed with a catalyst (Q1-cat).

Catalyst (Q1-cat) is selected from the group consisting of iodine, 1,2-dibromoethane, $TiCl_4$, $AlCl_3$, $PbCl_2$, $BiCl_3$, LiCl and mixtures thereof.

Preferably, reagent (Q3-reag) is water or aqueous $NH_4Cl$.

Preferably, reaction (Q1-reac) is performed in a solvent (Q1-solv).

Preferably, reaction (Q2-reac) is performed in a solvent (Q2-solv).

Preferably, reaction (Q3-reac) is performed in a solvent (Q3-solv).

Preferably, solvent (Q1-solv), solvent (Q2-solv) and solvent (Q3-solv) are identical or different and independently from each other selected from THF, methyl-THF, NMP, diethylether, methyl-tert-butylether, methoxycyclopentane, diisopropylether, 1,2-dimethoxyethane, tri $C_{1-4}$ alkyl amine and mixtures thereof;
more preferably from THF, 2-methyl-THF, 1,2-dimethoxyethane, methyl-tert-butylether, methoxycyclopentane, tri $C_{1-4}$ alkyl amine and mixtures thereof;
even more preferably from the group consisting of THF, 2-methyl-THF, 1,2-dimethoxyethane, triethylamine, and mixtures thereof.

Preferably the solvent (Q1-solv), solvent (Q2-solv) and solvent (Q3-solv) are identical.

The reaction temperatures of reaction (Q1-reac), of reaction (Q2-reac) and of reaction (Q3-reac) are identical or different and idependently from each other preferably from −100 to 150° C., more preferably from −60 to 100° C., and even more preferably from −20 to 80° C.

Reaction (Q1-reac), reaction (Q2-reac) and reaction (Q3-reac) can be done at a constant temperature, or the temperature may be modified during the progress of the reactions. For instance, the reactions can run for a certain time at first temperature, and then for a subsequent time at a second temperature different from the first temperature. Alternatively, the temperature may be modified continuously during the reaction.

The reaction times of reaction (Q1-reac), of reaction (Q2-reac) and of reaction (Q3-reac) are identical or different and idependently from each other preferably from 30 min to 48 h, more preferably from 1 to 24 h, even more preferably from 2 to 12 h.

The amounts of solvent (Q1-solv), of solvent (Q2-solv) and of solvent (Q3-solv) are are identical or different and idependently from each other preferably from 2 to 40 fold, more preferably from 3 to 10 fold, even more preferably from 5 to 7 fold, of the weight of compound of formula (XXV), of the weight of the reaction product of reaction (Q1-reac) and of the weight of the reaction product of reaction (Q2-reac) respectively.

Preferably, from 1.0 to 10 mol equivalents, more preferably from 1.1 to 5 mol equivalents, even more preferably from 1.1 to 3 mol equivalents of reagent (Q1-reag) are used, the mol equivalents being based on the mol of compound of formula (XXV).

Preferably, from 1.0 to 10 mol equivalents, more preferably from 1.1 to 5 mol equivalents, even more preferably from 1.1 to 3 mol equivalents of acetone are used, the mol equivalents being based on the mol of compound of formula (XXV).

Preferably, from 1.0 to 100 mol equivalents, more preferably from 1.1 to 50 mol equivalents, even more preferably from 1.1 to 30 mol equivalents of reagent (Q3-reag) are used, the mol equivalents being based on the mol of compound of formula (XXV) or of the mol of the reaction product of reaction (Q2-reac).

Preferably, reaction (Q1-reac), reaction (Q2-reac) and reaction (Q3-reac) are done at atmospheric pressure.

Preferably, reaction (Q1-reac), reaction (Q2-reac) and reaction (Q3-reac) are done under inert atmosphere. Preferably, the inert atmosphere is achieved by the use if an inert gas selected from the group consisting of argon, another noble gas, lower boiling alkane, nitrogen and mixtures thereof.

The lower boiling alkane is preferably a $C_{1-3}$ alkane, i.e. methane, ethane or propane.

After reaction (Q1-reac), reaction (Q2-reac) and reaction (Q3-reac), the reaction product of reaction (Q1-reac), the reaction product of reaction (Q2-reac) and compound of formula (XXIV) respectively can be isolated by standard methods such as evaporation of volatile components, extraction, washing, drying, concentration, crystallization, distillation, chromatography and any combination thereof.

Preferably, the reaction product of reaction (Q1-reac) and the reaction product of reaction (Q2-reac) are not isolated.

Preferably, reaction (Q1-reac), reaction (Q2-reac) and reaction (Q3-reac) are done consecutively; preferably, reaction (Q1-reac), reaction (Q2-reac) and reaction (Q3-reac) are done in one pot.

In another preferred embodiment, reaction (Q1-reac) and reaction (Q2-reac) can be done in one pot by adding reagent (Q1-reag) to a mixture of compound of formula (XXV) and acetone in a solvent (Q1-solv); reaction (Q3-reac) is done thereafter, preferably in the same pot.

Compound of formula (XXIV) is preferably isolated using conventional methods, such as evaporation of volatile components, hydrolysis and optional acidification of the higher-boiling residue, extraction, and distillation.

Any aqueous phase can be extracted, preferably the extraction is done with a solvent (Q-extract). Solvent (Q-extract) is benzene, toluene, ethyl acetate, or isopropyl acetate.

Any organic phase can be dried, preferably with magnesium sulphate.

Any concentration is preferably done by distillation, preferably under reduced pressure.

The compound of formula (XXIV) can be purified, preferably by crystallization or distillation under reduced pressure.

Medetomidine and compounds of formula (XXI) and (XXII) are chiral compounds, and the formulae comprise any enantiomer as well as any mixture of enantiomers of medetomidine, of the compounds of formula (XXI), or of formula (XXII) respectively. Enantiomers can be separated by conventional procedure known in organic chemistry, such as repeated crystallizations of the (+) tartaric acid salt in alcoholic media, as disclosed for medetomidine in Cordi et al., Synth. Commun. 1996, 26, 1585-1593.

Compounds of formula (XXV) are known compounds and can be prepared according to known methods.

The progress of any of the reactions reaction (M1-reac), reaction (M2-reac), reaction (N-reac), reaction (O-reac), reaction (O1-reac), reaction (O2-reac), reaction (P-reac), reaction (Q1-reac), reaction (Q2-reac) and reaction (Q3-reac) can be monitored by standard techniques, such as nuclear magnetic resonance spectroscopy (NMR), infrared spectroscopy (IR), High performance Liquid Chromatography (HPLC), Liquid Chromatography Mass Spectrometry (LCMS), or Thin Layer Chromatography (TLC), and work-up of the reaction mixture can start, when the conversion of the starting material exceeds 95%, or when no more starting material can be detected. The time required for this to occur will depend on the precise reaction temperature and the precise concentrations of all reagents, and may vary from batch to batch.

In general, any organic phase can be dried, preferably over $MgSO_4$ or $Na_2SO_4$, if not stated otherwise.

Compared to prior art, the method of the present invention offers several advantages: Importantly, the whole carbon framework of medetomidine is built in few chemical steps, using cheap reagents only. No protecting groups are needed and the overall amount of material used is therefore reduced, the batch size based on molar amounts is increased. In particular no trityl or acetal protection groups are used and no protection of the imidazoles is necessary. Thereby the number and amount of reagents needed is reduced, and no protecting or deprotecting steps being needed the waste is reduced, contrary to when for example a trityl or acetal protecting group is used. The method has good yields.

EXAMPLES

Methods $^1H$ and $^{13}C$ NMR spectra were recorded on a Varian VNMRS 500 (500 MHz for $^1H$ and 125 MHz for $^{13}C$) instruments in $CDCl_3$. Chemical shifts are expressed in parts per million referred to TMS and coupling constants (J) in hertz.

EI means Electron ionization mass spectra (70 eV), they were obtained on an AMD-604 spectrometer.

ESI means Electron spray ionization mass spectra

THF was distilled from sodiumbenzophenone ketyl prior to use; the obtained anhydrous THF is called "dry THF" in the following text.

Example 1

2-(2,3-Dimethylphenyl)Propan-2-ol, Compound of Formula (XXIV), Prepared via an Organomagnesium Intermediate 1-Bromo-2,3-dimethylbenzene (compound of formula (XXV), wherein Q is Br; 8.43 g, 45.6 mmol) was dissolved in dry THF (15 mL) and placed in dropping funnel. Separately, Mg wire (1.10 g, 45.3 mmol) in dry THF (5 mL) was placed in a flask equipped with the above mentioned dropping funnel, a stirrer, and a reflux condenser. The 1-bromo-2,3-dimethylbenzene solution (1.0 mL) was added via a dropping funnel and the reaction was initiated by the addition of 1,2-dibromoethane (3 drops), and then the rest of the 1-bromo-2,3-dimethylbenzene solution was added. The content of the dropping funnel was added at such a rate to maintain slight reflux. After completion of the addition, the mixture was refluxed for 1 h and then cooled to 0° C. A solution of dry acetone (4.2 mL, 58 mmol) in dry THF (15 mL) was added dropwise and the mixture was stirred at a temperature between 0 and 20° C. for 3 h. The mixture was poured into saturated $NH_4Cl$ aqueous solution (100 mL) extracted with hexane (5 times with 50 mL each), dried with $Na_2SO_4$ and evaporated under reduced pressure. The main product was isolated via silica gel column chromatography with hexane:ethyl acetate as eluent (v/v 15:1 to 10:1 gradient), to yield 3.50 g (47%) of the title compound. $^1H$ NMR: 1.68 (s, 6H), 1.70 (s, 1H), 2.29 (s, 3H), 2.50 (s, 3H), 7.03 to 7.10 (m, 2H), 7.29 to 7.32 (m, 1H).

$^{13}C$ NMR: 17.72, 21.08, 31.24, 73.71, 123.11, 125.02, 129.02, 135.09, 138.69, 145.47. MS (EI): 164 (12), 149 (35), 146 (100), 131, 116, 105, 91.

Example 2

2-(2,3-Dimethylphenyl)Propan-2-ol, Compound of Formula (XXIV), Prepared via an Organolithium Intermediate 1-Bromo-2,3-dimethylbenzene (compound of formula (XXV), wherein Q is Br; 4.25 g, 23.0 mmol) was dissolved in dry THF (20 mL) in a flask equipped with a thermometer and a stirring bar. The mixture was cooled to −78° C. n-Butyl-lithium (1.6 M in hexane, 17.5 mL, 28.0 mmol) was added dropwise via a syringe, keeping the temperature below −70° C. When the addition was complete, the mixture was maintained at −78° C. and stirred at this temperature for 1 h. A solution of dry acetone (1.85 mL, 25.2 mmol) in dry THF (5 mL) was then added at −78° C. The mixture was stirred at −78° C. for 30 min, the cooling bath was removed, and the mixture was allowed to reach room temperature. The mixture was poured into saturated aqueous $NH_4Cl$ solution (100 mL), extracted with hexane (4 times with 50 mL each), dried over $Na_2SO_4$, and purified by via silica gel column chromatography using hexane:ethyl acetate as eluent (vv 32:1) to give 3.45 g (91%) of the title compound. The measured NMR spectra were identical to those recorded in example 1.

Example 3

1,2-Dimethyl-3-(2-propenyl)benzene, compound of formula (XXIII)

2-(2,3-Dimethylphenyl)propan-2-ol, compound of formula (XXIV), prepared according to either example 1 or example 2, (1.10 g, 6.70 mmol), was dissolved in benzene (20 mL), and p-toluenesulfonic acid monohydrate (35 mg, 0.18 mmol) was added. The mixture was stirred at room temperature for 3 h. Silica gel (200 mg) was added, and stirring was continued for ca. 16 hours, and then the reaction mixture was refluxed for 30 min. After cooling to room temperature, the mixture was filtered, washed with aqueous $K_2CO_3$ solution, conventionally dried, and concentrated under reduced pressure, to yield 0.90 g (92%) of the title compound. $^1$H NMR: 2.02 (m, 3H), 2.21 (s, 3H), 2.28 (s, 3H), 4.82 (m, 1H), 5.17 (m, 1H), 6.97 (m, 1H), 7.05 (m, 2H).

Example 4

2-(2,3-Dimethylphenyl)Methyloxirane, Compound of Formula (XXII)

A buffer was prepared by dissolving $K_2CO_3$ (20.7 g) and $EDTA-Na_2$ (11.5 mg) in water (100 mL). 1,2-Dimethyl-3-(2-propenyl)benzene, compound of formula (XXIII), prepared according to example 3 (0.90 g, 6.16 mmol), was dissolved in a mixture of dichloromethane and acetonitrile (vv 1:1, 60 mL), and the buffer prepared as described above (9.3 mL) was added. To the resulting mixture, first 1,1,1-trifluoroacetone (60 μL) and then hydrogen peroxide (30% in water, 6.2 mL, 60.7 mmol) were added and the mixture was stirred at room temperature for 2 h. The reaction mixture was diluted with water (100 mL), the organic phase was separated, and the aqueous phase was extracted with dichloromethane (2 times with 50 mL each). The combined organic phases were dried over $Na_2SO_4$, concentrated under reduced pressure, and the residue was purified by via silica gel column chromatography using hexane:ethyl acetate as eluent (vv 32:1) to give 851 mg (85%) of the title compound.

$^1$H NMR: 1.59 (s, 3H), 2.28 (s, 3H), 2.31 (s, 3H), 2.83 (br d, J=5.4, 1H), 2.98 (d, J=5.4 Hz, 1H), 7.08 (m, 2H), 7.21 (m, 1H).

MS (EI): 162, 147, 133, 117 (100).

Example 5

2-(2,3-Dimethylphenyl)Propanal, Compound of Formula (XXI)

2-(2,3-Dimethylphenyl)methyloxirane, compound of formula (XXII), prepared according to example 4 (0.84 g, 5.18 mmol), was dissolved in dry dichloromethane (50 mL) and powdered $Cu(BF_4)_2$ hydrate (318 mg) was added at room temperature. After 2 h at room temperature, the mixture was washed with water, dried over $Na_2SO_4$ and concentrated under reduced pressure to yield 0.84 g (100%) of the title product.

$^1$H NMR: 1.40 (d, J=7.1 Hz, 3H), 2.25 (s, 3H), 2.32 (s, 3H), 3.89 (qd, J=7.1, 1.0 Hz, 1H), 6.89 to 6.92 (m, 1H), 7.12 (m, 2H), 9.67 (d, J=1.0 Hz, 1H).

Example 6

Medetomidine 2-(2,3-Dimethylphenyl)propanal, compound of formula (XXI), prepared according to example 5 (2.43 g, 15.0 mmol) and p-toluenesulfonylmethyl isocyanide (2.73 g, 14.0 mmol) were mixed with EtOH (30 mL). To the stirred suspension powdered NaCN (73 mg, 1.5 mmol) was added. The mixture was stirred for 1 h at room temperature, and then evaporated under reduced pressure to dryness. The residue was placed in an ampoule and treated with MeOH saturated with $NH_3$ (50 mL). The ampoule was heated to 110° C. in an oil bath for three days.

This experiment was repeated once more (2-(2,3-Dimethylphenyl)propanal: 3.24 g, 20.0 mmol; p-toluenesulfonylmethyl isocyanide: 3.90 g, 20.0 mmol).

Both reaction mixtures were combined, evaporated to dryness, dissolved in dichloromethane (150 mL) and washed with 10% (w/w) aqueous $Na_2CO_3$ (200 mL) and then with water (200 mL), conventionally dried, evaporated under reduced pressure and purified by via silica gel column chromatography using dichloromethane : methanol as eluent (v/v 15:1 to 10:1 gradient), to yield 3.0 g (44%) of medetomidine as a sticky oil. Medetomidine was crystallized from toluene:cyclohexane, and then recrystallized from aqueous ethanol.

$^1$H NMR: 1.56 (d, J=7.2 Hz, 3H), 2.18 (s, 3H), 2.25 (s, 3H), 4.35 (q, J=7.2 Hz, 1H), 6.66 (s, 1H), 6.93 (dd, J=6.6, 2.2 Hz, 1H), 6.99 to 7.05 (m, 2H), 7.30 (d, J=1.1 Hz, 1H), 9.84 (broad s, 1H).

$^{13}$C NMR: 14.65, 20.72, 20.88, 14.12, 117.61, 124.62, 125.53, 127.91, 134.05, 134.60, 136.76, 141.11, 143.23.

MS (ESI): 201 [M+H]$^+$

The invention claimed is:

1. A method for the preparation of medetomidine, the method comprises a step (N) and a step (M1); step (M1) comprises a reaction (M1-reac); reaction (M1-reac) is a reaction between a compound selected from the group consisting of a compound of formula (XXI), a hydrate of the compound of formula (XXI) and a hemiacetal of the compound of formula (XXI),

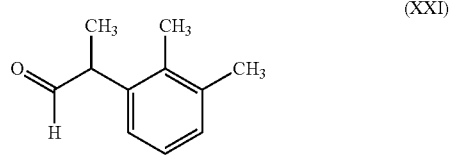

said hemiacetal of the compound of formula (XXI) being the product of an addition reaction between the aldehyde as depicted in formula (XXI) and an alcohol selected from the group consisting of test-butanol and isopropanol, and a reagent (M-reag) and a reagent (M-A) in a solvent (M-solv);

reagent (M-reag) is selected from the group consisting of p-toluenesulfonylmethyl isocyanide, trifluoromethanesulfonylmethyl isocyanide, methanesulfonylmethyl isocyanide, benzenesulfonylmethyl isocyanide, 4-acetamidobenzenesulfonylmethyl isocyanide and mixtures thereof;

reagent (M-A) is selected from the group consisting of ammonia, sulfamic acid, p-toluenesulfonamide, benzenesulfonamide, 4-acetamidobenzenesulfonamide, tritylamine, formamide, urea, urotropine, ethyl carbamate, acetamide and mixtures thereof;

solvent (M-solv) is selected from the group consisting of N,N-dimethylformamide, $C_{1-6}$alkanol, formamide, 1,2-dimethoxyethane, NMP, toluene, acetonitrile, propionitrile, ethyl carbamate, N,N-dimethylacetamide, water, acetamide and mixtures thereof;

and wherein the compound of formula (XXI) is prepared in the step (N);

step (N) comprises a reaction (N-reac);

reaction (N-reac) is a reaction of a compound of formula (XXII) with a catalyst (N-cat);

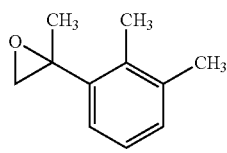 (XXII)

catalyst (N-cat) is selected from the group consisting of acetic acid, formic acid, trifluoroacetic acid, methanesulfonic acid, benzenesulthnic acid, p-toluenesulfonic acid, camphorsulfonic acid, HCl, HBr, $H_2SO_4$, $HNO_3$, $H_3PO_4$, $HClO_4$, $BCl_3$, $BBr_3$, $BF_3OEt_2$, $BF_3SMe_2$, $BF_3THF$, $MgCl_2$, $MgBr_2$, $MgI_2$, $AlCl_3$, $Al(O-C_{1-4}$ alky$)_3$, $SnCl_4$, $TiCl_4$, $Ti(O-C_{1-4}$ alkyl$)_4$, $ZrCl_4$, $Bi_2O_3$, $BiCl_3$, $ZnCl_2$, $PbCl_2$, $FeCl_3$, $ScCl_3$, $NiCl_2$, $Yb(OTf)_3$, $Yb(Cl)_3$, $GaCl_3$, $AlBr_3$, $Ce(OTf)_3$, LiCl, $Cu(BF_4)_2$, $Cu(OTf)_2$, $NiBr_2(PPh_3)_2$, $NiBr_2$, $NiCl_2$, $Pd(OAc)_2$, $PdCl_2$, PtCl, $InCl_3$, acidic inorganic solid substance, acidic ion exchange resin, carbon treated with inorganic acid and mixtures thereof.

2. The method according to claim 1, wherein
reaction (M1-reac) is a reaction between
a compound of formula (XXI) or the hydrate of the compound of formula (XXI),

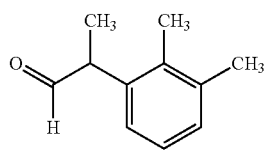 (XXI)

and a reagent (M-reag) and a reagent (M-A) in a solvent (M-solv).

3. The method according to claim 1, wherein
reaction (M1-react)is a reaction between
a compound of formula (XXI),

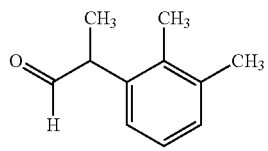 (XXI)

and a reagent (M-reag) and a reagent (M-A) in a solvent (M-solv).

4. The method according to claim 1, wherein reagent (M-reag) is selected from the group consisting of p-toluenesulfonylmethyl isocyanide, benzenesulfonyimethyl isocyanide and mixtures thereof.

5. The method according to claim 1, wherein reagent (M-A) is selected from the group consisting of ammonia, sulfamic acid, p-toinenesulfonamide, benzenesulfonamide, 4-acetamidobenzenesulfonamide, tritylamine, formamide and mixtures thereof.

6. The method according to claim 1, wherein solvent (M-solv)is selected from the group consisting of N,N-dimethylformamide, methanol, ethanol, n-propanol, isopropanol, butanol, pentanol, hexanol., water, formamide, 1,2-dimethoxyethane, NMP, toluene, acetonitrile, propionitrile, ethyl carbamate, N,N-dimethylacetamide, acetamide and mixtures thereof.

7. The method according to claim 1, wherein reaction (M1-reac) is done in the presence of a compound (M-comp), compound (M-comp) is selected from the group consisting of ammonia, tritylamine, NaCN, KCN, piperidine, DBU, DABCO, triethylamine, tributylamine, 4-dimethylaminopyridine, pyridine, tBuOK, tBuONa, $NaHCO_3$, $Na_2CO_3$, $(NH_4)HCO_3$, $(NH_4)_2CO_3$, $KHCO_3$, $K_2CO_3$, NaOAc, KOAc, NaOH, KOH, $Ca(OH)_2$, KF and mixtures thereof.

8. The method according to claim 7, wherein compound (M-comp) is selected from the group consisting of ammonia, tritylamine, NaCN, KCN, piperidine, tBuOK, tBuONa, KOH, $K_2CO_3$, $Na_2CO_3$, KF and mixtures thereof.

9. The method according to claim 1, wherein the compound of formula (XXI) is first reacted with the reagent (M-reag) and then the reagent (M-A) is added;
or
compound of formula (XXI) is first reacted with the reagent (M-A) and then the reagent (M-reag) is added;
or
compound of formula (XXI) is simultaneously reacted with the reagent (M-reag) and with the reagent (M-A).

10. The method according to claim 1, wherein the catalyst (N-cat) is selected from the group consisting of acetic acid, formic acid, trifluoroacetic acid, methanesulfonic acid, p-toluenesulfonic acid, HCl, HBr, $H_2SO_4$, $H_3PO_4$, $BCl_3$, $BF_3OEt_2$, $MgCl_2$, $MgBr_2$, $AlCl_3$, $ZnCl_2$, $Cu(BF_4)_2$, aluminosilicates, acidic ion exchange resins, carbon treated with HCl, $H_2SO_4$ or $HNO_3$, and mixtures thereof.

11. The method according to claim 1, wherein reaction (N-reac) is done in a solvent (N-solv);
solvent (N-solv) is selected from the group consisting of water, tert-butanol, isopropanol, acetonitrile, propionitrile, THF, methyl-THF, NMP, dioxane, 1,2-dimethoxyethane, dichloromethane, 1,2-dichloroethane, chloroform, toluene, benzene, chlorobenzene, hexane, cyclohexane, ethyl acetate, acetic acid, formic acid, trifluoroacetic acid and mixtures thereof.

12. The method according to claim 1, wherein compound of formula (XXII) is prepared in a step (O) or in two steps, the two steps are step (O1) and step (O2);
step (O) comprises a reaction (O-reac);
reaction (O-reac)is a reaction of a compound of formula (XXIII), with a reagent (O-reag);

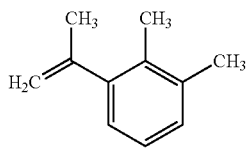 (XXIII)

reagent (O-reag) is selected from the group consisting of peracetic acid, trifluoroperacetic acid, perhenzoic acid, 3-chloroperbenzoic acid, monoperphthalic acid, dimethyldioxirane, tent-butylhydroperoxide, dibenzoyi peroxide, cumenehydroperoxide, oxygen, air, sodium hypochlorite, $KHSO_5$, $Na_2O_2$, aqueous $H_2O_2$, $H_2O_2$ dissolved in acetic acid, $H_2O_2$ dissolved in trilluoroacetic acid, and mixtures thereof;
step (O1) comprises a reaction (O1-reac);

reaction (O1-reac) is a reaction of a compound of formula (XXIII) with water and with a compound (O1-comp) to provide a reaction product from reaction (O1-reac);
compound (O1-comp) is selected from the group consisting of bromine, N-bromosuccinimide, chlorine, N-chlorosuccinimide, iodine, N-iodosuccinimide, IBr, BrCl, and mixtures thereof;
step (O2) comprises a reaction (O2-reac);
reaction (O2-rear) is a reaction of the reaction product from reaction (O1-reac) with a base (O2-base);
base (O2-base) is selected from the group consisting of sodium hydroxide, potassium hydroxide, calcium hydroxide and mixture thereof.

13. The method according to claim 12, wherein reagent (O-reag) is selected from the group consisting of peracetic acid, tort-butylhydroperoxide, oxygen, air, sodium hypochlorite, aqueous $H_2O_2$, $H_2O_2$ dissolved in acetic acid, $H_2O_2$ dissolved in trifluoroacetic acid, and mixtures thereof.

14. The method according to claim 12, wherein the compound of formula (XXIII) is prepared in a step (P);
step (P) comprises a reaction (P-reac);
in reaction (P-reac) a compound of formula (XXIV) is exposed to a temperature (P-temp);

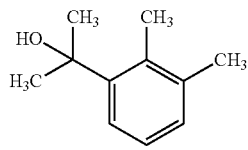

(XXIV)

temperature (P-temp) is from 0 to 300° C.

15. The method according to claim 14, wherein the compound of formula (XXIV) is prepared in three steps, the three steps are a step (Q1), a step (Q2) and a step (Q3);
step (Q1) comprises a reaction (Q1-reac) by a reaction of a compound of formula (XXV) with a reagent (Q1-reag) to provide a reaction product of reaction (Q1-reac);

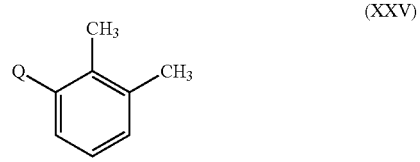

(XXV)

Q is Br, Cl, or I;
reagent (Q1-reag) is selected from the group consisting of lithium, magnesium, aluminum, zinc, calcium, isopropylmagnesium chloride, isopropyimagnesium bromide, butyllithium, sec-butyllithium and mixtures thereof;
step (Q2) comprises a reaction (Q2-reac);
reaction (Q2-reac) is a reaction of the reaction product of reaction (Q1-reac) with acetone to provide a reaction product of reaction (Q2-reac);
in step (Q3) comprises a reaction (Q3-reac);
reaction (Q3-reac) is a reaction of the reaction product of reaction (Q2-reac) with a reagent (Q3-reac);
reagent (Q3-reag) is selected from the group consisting of water, methanol, ethanol, oxalic acid, citric acid, $NH_4Cl$, HCl, HBr, $HNO_3$, $H_2SO_4$, $H_3PO_4$ acetic acid, propionic acid, formic acid and mixtures thereof.

* * * * *